Figure 1:
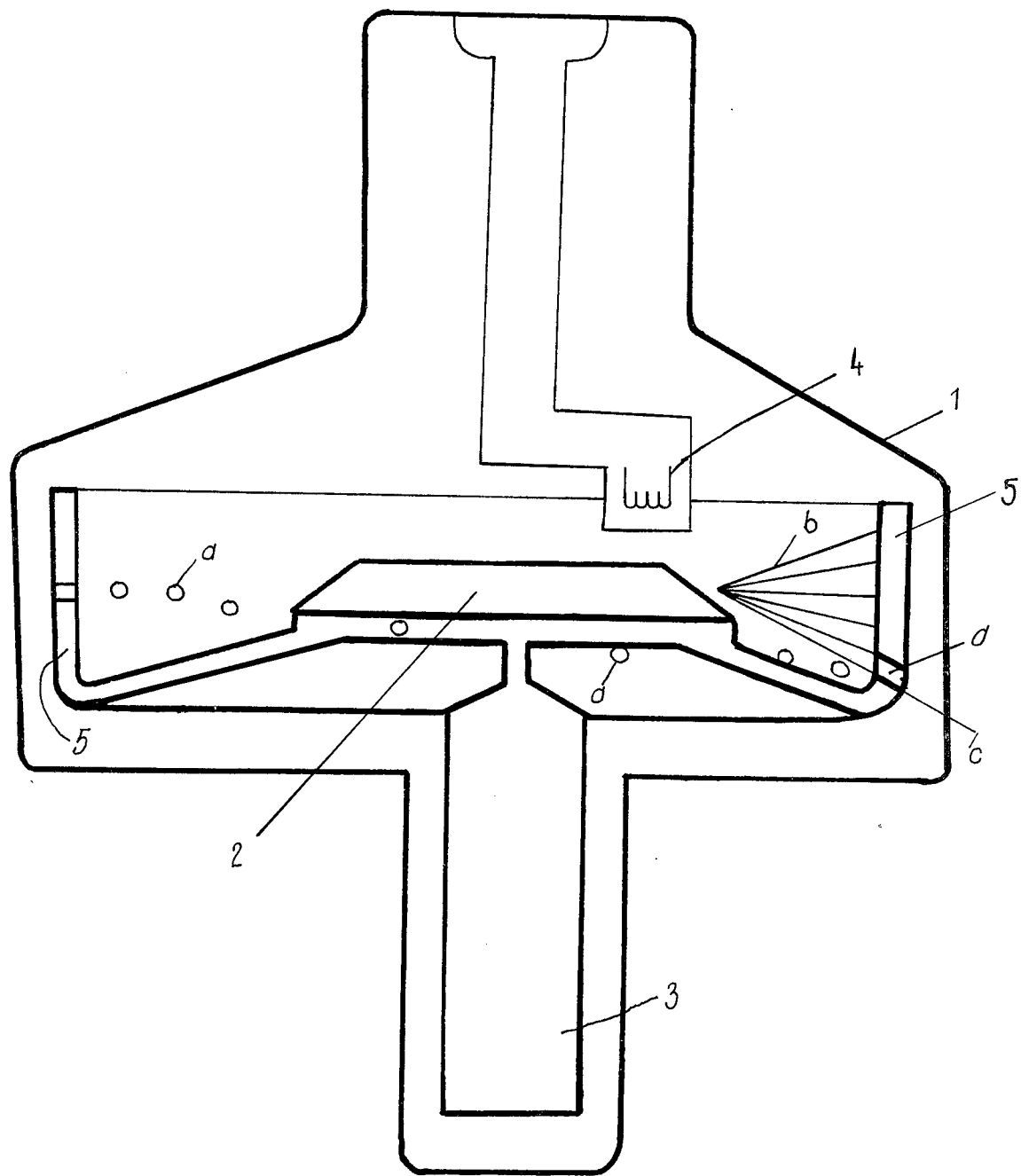

United States Patent [19]

Voinea et al.

[11] 4,234,794
[45] Nov. 18, 1980

[54] INSTALLATION OF RADIODIAGNOSIS WITH SWEEP

[75] Inventors: Vasile Voinea; Vasile Catuneanu; Ioan Birzu; Eugen Teisanu; Maria I. Voinea; Sorin Patrascu, all of Bucharest, all of Romania

[73] Assignee: Statia de Verificare si Intretinere a Aparaturii Medicale, Bucharest, Romania

[21] Appl. No.: 962,153

[22] Filed: Nov. 20, 1978

[30] Foreign Application Priority Data

Dec. 22, 1977 [RO] Romania .................................. 92587

[51] Int. Cl.³ ............................................. H05G 1/70
[52] U.S. Cl. .............................. 250/416 TV; 250/406; 250/445 T; 250/505
[58] Field of Search ................ 250/416 TV, 401, 402, 250/406, 445 T, 505

[56] References Cited

U.S. PATENT DOCUMENTS

| 2,638,554 | 5/1953 | Bartow | 250/416 TV |
| 2,667,585 | 1/1954 | Gradsteen | 250/416 TV |
| 2,730,566 | 1/1956 | Bartow | 250/416 TV |
| 2,825,817 | 3/1958 | North | 250/416 TV |
| 2,837,657 | 6/1958 | Craig | 250/416 TV |

Primary Examiner—Craig E. Church
Attorney, Agent, or Firm—Karl F. Ross

[57] ABSTRACT

The installation according to the invention practically eliminates the total irradiation of the radiologic examinated persons, using an X radiations source, which produces a swept filiform beam, synchronized with the sweep of a T.V. monitor. In this way the useless irradiation of the entire examined surface is avoided with a strict exception of a single image point useful at one given moment, image point which is transmitted to the T.V. monitor.

There are given more achievement variants of the swept filiform beam, as: radioopaques screens with punctiform orifices or slits and radiodiagnosis tubes with swept emission point of the X radiation associated with antidiffusion grids which turn the swept X radiations beam into a swept filiform X radiations beam.

The radiodiagnosis tube with swept emission point of the X radiations is utilized also for the achievement of a tomoscopy or an electronic tomography with the wipe in surface. In this purpose the desirable plane of the examined object is selected by adjustment of the sweep on the T.V. monitor by means of a supplementary deflexion system.

7 Claims, 12 Drawing Figures

INSTALLATION OF RADIODIAGNOSIS WITH SWEEP

The invention refers to an installation of radiodiagnosis with T.V. chain, wich asures the reduction of the irradiation of the examined persons and of the attending staff, improves the radiologic image, achieves a tomographic image with wipe into the surface of the images of the opacities from the undesired layers; it is utilized for medical and technical examinations.

There are known installations of radiodiagnosis having radiodiagnosis tubes with rotary anode and T.V. chain.

These installations have the disadvantage of the continuous irradiation of the whole volume of the examined object, although at one time it is transmited only a single point image from the radiosensitive surface to the T.V. monitor. This irradiation, except of a filiform beam of which punctiform image is transmised by the T.V. chain is useless and leads to massive and no justifiable irradiation of the examined body. Another disadvantage is the great number of the radiologic image transformations: X radiations into photoelectrons, acceleration of the photoelectrons in the image amplifier, formation of a reduced fluoroescent image on the secondary screen, sweep of the reduced image in the camera, and its increase again in the T.V. monitor. The ensemble of these transformations leads to the distorsion of the image and the decrease of the resolution power. Another disadvantage is the great size of the focus of the radiodiagnosis tube what also decreases the power of resolution. Another disadvantage is the complex mechanic and electronic character of the installation what leads to a high cost price, reduced reliability and difficult maintenance.

Also there are known tomographs with mobile radiodiagnosis tube with a displacement of the radiations source in a right or other formline direction.

Also there are known polytomographs with which, by a single exposition to X radiations there are obtained more tomographic images on different radiographic films.

These tomographs and polytomographs have the disadvantages that they achieve a linear wipe of the opacities from the undesirable layers after a right or an other formeline, which wipe, often is insufficient and it creates artifacts.

The complex curves utilization for the wipe of the image of the opacities from the undesirable layers lead to the increase of the exposition time and the worsening of the image quality. These tomographs and polytomographs have a further disadvantage, that they have mobile, mechanic, hard manipulated components, for what reason the large majority of the set up tomographs are not utilized.

Also the computered tomograph is known, which achieves an axial tomography, the image being taken over by the scintillator elaborated by the computer, displied by the monitor and photographed. The computered tomography has also the disadvantage of a linear wipe. Another disadvantage of the computered tomograph is the great complexity and the high cost price.

The main object of the present invention is the creation of an installation of radiodiagnosis with an simplified T.V. chain, in which a X radiations filiform beam is obtained, which irradiate exclusively the image point of the examined object in each moment and is transmited from the radiosensitive surface to a T.V. monitor, removing entirely the useless irradiation of the examined surface rest.

Another object of the present invention is the reduction of the secondary radiations quantity and the obtainment of an improved radiologic image.

To eliminate the disadvantages and the achievement of the mentioned objects, and installation according to the invention is equipped with a radiodiagnosis tube including in its inner a cathode, a rotary anode and a mobile radioopaque device made up of one or more pieces of cylindric, conic, discoid form or another geometric form, foreseen with punctiform orifices, situated on an helicoid line with one or more coils, or pieces foreseen with slits linear or other forms so that by their displacement a X radiations filiform swept beam is achieved, the mobile radioopaque device can make body with the rotary anode or can be acted by one or more electrical engines, the movement of the mobile radioopaque device being synchronized with the sweep of a T.V. monitor, with the aid of a synchronising system, the swept radiations beam after passage through the examined object is turned into video-signals by a translator, which can be an image amplifier with T.V. camera, a scintillator with photomultipllier or another known translator, wich video-signals after passage through an amplification system order the image formation in the T.V. monitor, in another variant it is used a conventional radiodiagnosis tube with a rotary anode and a mobile radioopaque device intended to achieve a swept filiform X radiations beam, wich radioopaque device is situated outside the radiodiagnosis tube or outside the radiodiagnosis tube cupola and in a third variant a part of the radioopaque device is situated in radiodiagnosis tube inner, and another part is situated outside the radiodiagnosis tube, also the disadvantages can be eliminated by achievement of another swept installation variant equiped with a radiodiagnosis tube, taking in its inner an electronic gun, a focusing system of the electrons flow, a deflexion system, which deflexion system can be symmetric or asymetric, a control grid and a fixed anode, the intensity of electrons flow being adjusted with the aid of the control grid by a control system according to a correction programme, the filiform electrons beam being swept on the fixed anode, which fixed anode is made-up of a metal with high atomic weight and high melting point, which fixed anode has plane, concave or another relief, bombarded surface which, alone or together with the control grid tends to the homogenizing of the X radiations flow, which X radiations flow arrive at the radiosensitive surface of an X radiations translator into light radiations and these into video-signals or X radiations into video-signals, after the X radiations emited by the fixed anode went through one or more antidiffusion systems, which antidiffusion systems can be fixed or mobile, situated between the fixed anode and examined object, inside or outside of the radiodiagnosis tube, every antidiffusion system being formed of one or more antidiffusion grids made-up of lamellas, fibres or tubes of high atomic weight substances or containing high atomic weight substances and having long and thin spaces, permeable for X radiations, the long and thin spaced having the axle directed so that it passes through the points of the fixed anode, swept by the electrons filiform beam, which axle passes also through the corresponding points of image of the examined object, a second variant of obtaining of the swept filiform X radiations beam uses a radioopaque plate, which has a punctiforme orifice, one or more antidiffusion systems placed between the fixed anode and the radioopaque plate and/or between the radioopaque plate and the examined object, the radioopaque plate and the antidiffusion systems being placed either in the radiodiagnosis tube or outside the radiodiagnosis tube, the antidiffusion system being formed of one or more antidiffusion grids, which antidiffusion grids are made up of lamellas, fibres or tubes of substances with high atomic weight or containing substances with high atomic weight, which antidiffusion grids have long and thin spaces permeable for X radiations, the permeable spaces have the axle oriented so that it passes through the centre of the punctiform orifice of the radioopaque plate and respectively through the points from the fixed anode swept by the filiform electrons beam, thus it is obtained a filiform X radiations beam, which filiform beam would not be obtained by means only of the single radioopaque plate with punctiform orifice, without antidiffusion systems, in both possibilities of obtaining of the filiform X radiations beam one can too add optionally one or more antidiffusion systems, placed between the examined object ant the radiosensitive surface of the T.V. chain, these antidiffusion systems being formed similarly with the other antidiffusion systems situated between the fixed anode and the examined object and having permeable spaces for X radiations orientated corresponding to the first respectively the second posibility of obtaining of the filiform X radiations beam, above described, also one can add obtionaly in both posibilities of obtaining of the filiform X radiations beam, an antidiffusion system placed in contact with the sensitive surface of the T.V. chain, wich antidiffusion system is made-up of optic fibres of cylindric, tubular, prismatic or another form, which optic fibres are made-up of substances with high atomic weight, having in the inner and between them long and thin spaces, containing luminiscent substances, the image obtained being taken over by the sensitive surface of the T.V. chain, the video signals being amplified with the aid of an amplifier and inserted into a T.V. monitor of which sweep of the electrons beam is synchronised with the sweep of the filiform electrons beam of the radiodiagnosis tube, with aid of a syncronisation generator, the radiodiagnosis installation according to the invention can be used too for the achievement of tomoscopies and tomographies with X radiations sweep, the installation being made-up in this purpose by a radiodiagnosis tube, having a cathode, a Wehnelt cylinder, a focussing and acceleration system, a grid, a deflection system of the electrons beam, and a fixed anode on which arrive the horizontal and upright sweep of the electrons beam, from the fixed anode the X radiations with swept point of emission arise, the electrons beam sweep can be achieved too, by the well-known possibilities used in the electronic microscope, the X radiations with swept point of emission pass through the examined object and arrive at a photocathode of an image amplifier with T.V. camera, which T.V. camera transforms the X radiations into videosignals, which are amplifiated into an amplification system and order the image into a T.V. monitor, the X radiations can reach after the passing of the examined object on the sensitive surface of another sort of translator of X radiations into video signals, the installation comprise too a first system of syncronising, which syncronises the cathodic beam sweep of the camera with the cathodic beam of the T.V, monitor, which T.V. monitor is provided with a supplementary deflection system, which displaces horizontally and verticaly the whole obtained image, in the inverse direction with respect to the displacement of the image from the T.V. camera respective from the T.V. monitor, the displacement achieved by the supplementary deflection system is syncronized with the electrons beam sweep focused from the radiodiagnosis tube by the second system of syncronizing and it has both in horizontal direction and vertical direction an inverse sense with respect to this sweep, the amplitude of the horizontal and vertical displacement achieved by the supplementary system of deflection can be adjusted by known possibilities, the displacement of the whole image can be achieved too by a deflection supplementary system set-up in the T.V. camera.

We give below nine examples of achievement, in connection with FIGS. 1–12.

The 1st example with reference to FIG. 1 which is a principle scheme of the radiodiagnosis tube, according to the invention, into a first form of achievement of the invention. The radiodiagnosis tube 1 is made up of glass, in which inner there are a rotary anode 2 a rotor 3, which makes body with the rotary anode 2, a cathode 4, a cylinder 5, of metal with heigh atomic weight and high melting point, which cylinder 5, makes body with the rotary anode 2. The cylinder 5 presents punctiform orifices a, placed along of an helicoid line. The number of punctiform orifices a, is equal with the number of lines from the sweep system of a T.V. monitor (non-represented). On the rotary anode 2 a conic beam of X radiations b arises. The orifices a of the cylinder 5 allow to pass a filiform beam c swept during of the passing of the orifices a in front of the conic beam of X radiations b. The swept filiform radiations pass through the examined object and said X radiations reach the sensitive surface of a scintilator with photomultiplier (non represented) where the X radiations are turned into video signals, which after amplification order the image of a T.V. monitor (non-represented). The sweep of the filiform X radiations beam is synchronized with the sweep of the T.V. monitor through a device of synchronizing (non-represented).

Figure 2:
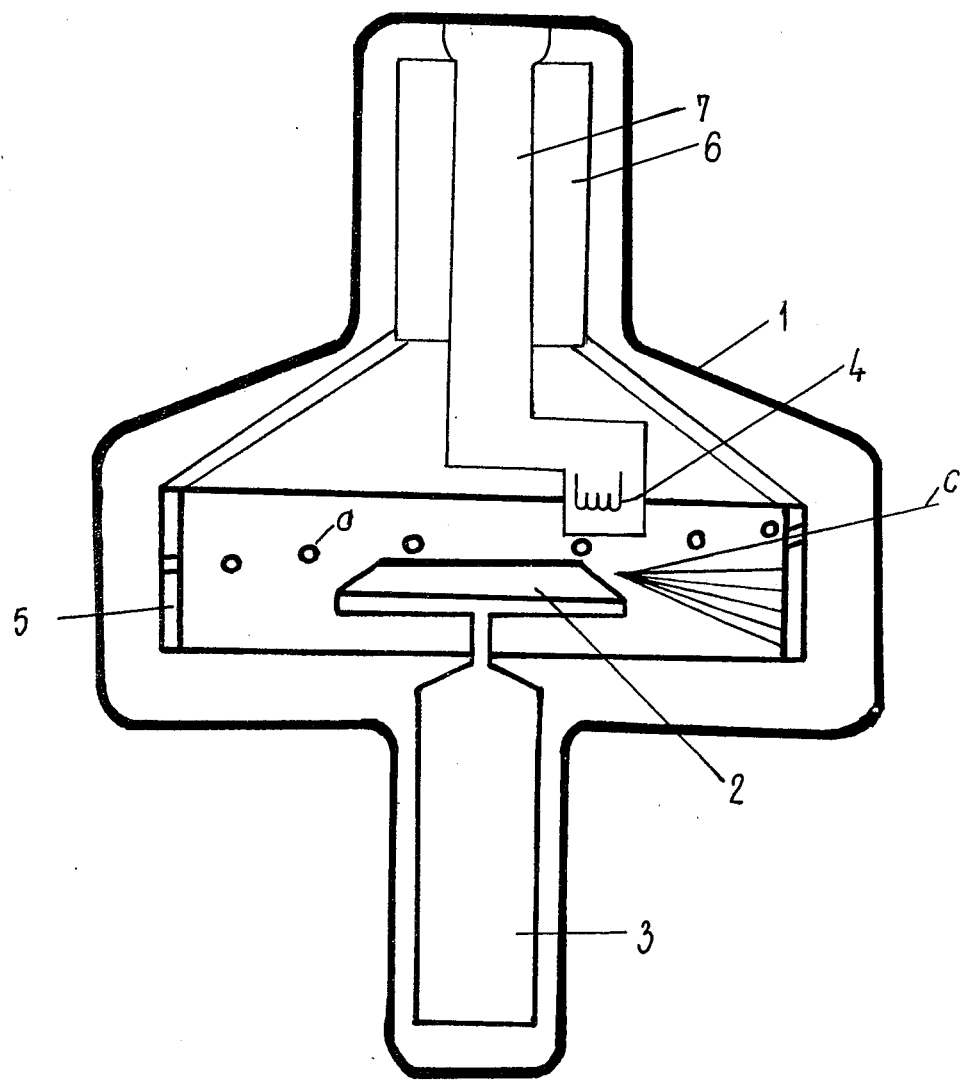

The 2nd example in connection with FIG. 2 which represents a principle scheme of the radiodiagnosis tube according to the invention in a second form of achievement. The radiodiagnosis tube 1 is made-up of glass in which inner there is a rotary anode 2, a rotor 3 which makes body with the rotary anode 2, a cathode 4, a cylinder 5 of metal with high atomic weight and high melting point, which cylinder 5 makes common body with a second rotor 6 of a second electric engine, the rotor 6 being situated in the inner of the radiodiagnosis tube 1, which rotor 6 wheels roud a support 7 of the cathode 4 through rollings. The cylinder 5 presents punctiform orifices a, placed along of a helicoid line, the number of the punctiform orifices a being equal with the number of lines from the system of sweep of a T.V. monitor (non-represented) the operation way of the radiodiagnosis tube according to the second example is identical with that of the first example, with the difference that the rotor 6 wheels round with a different rate with respect to the rotor 3 of the rotary anode 2. The achieving form of the invention described in the second example is utilized in cases when the rotation rate of the cylinder 5 and therefore the rotation rate of the sweep system does not correspond to the rotation rate of the rotary anode 2.

Figure 3:
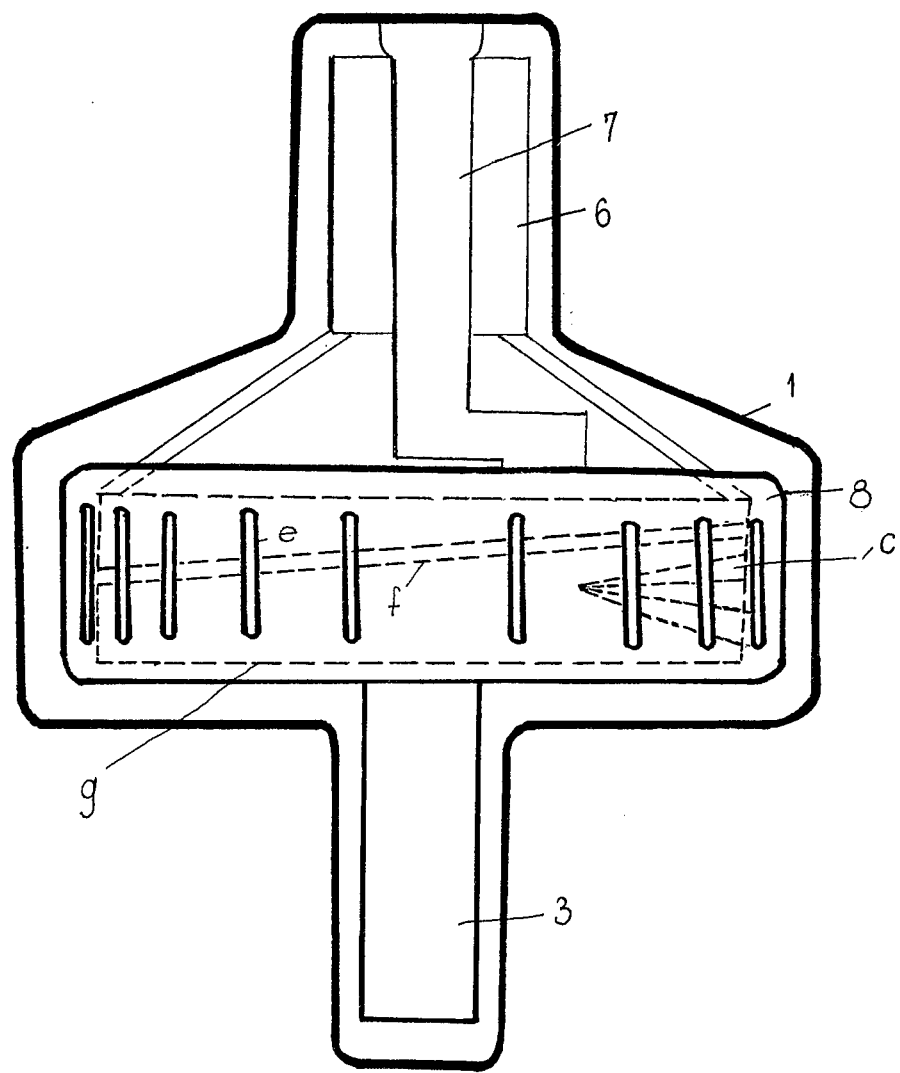

The 3d example in connection with FIG. 3, which represents a principle scheme of the radiodiagnosis tube, according to the invention into a third form of achievement. A radiodiagnosis tube 1 is made-up of glass in which inner there are a rotary anode 2, a rotor 3 which makes body with the rotary anode 2, a cathode 4, an outer cylinder 8 made-up of a metal with high atomic weight and high melting point, which outer cylinder 8 makes common body with the rotary anode 2. This outer cylinder 8 presents parallel linear slits e, which slits allow the exclusive passing of a X radiations lamellar beam. The number of said slits is so calculated as depending of the angular rate of the rotary anode 2 to realize the number of horizontal lines of the image from thr T.V. monitor. The second inner cylinder 9 is made-up of a metal with high atomic weight and high melting point and is placed into the inner of the outer cylinder 8. The inner cylinder 9 makes common body with a rotor 6 of the second electric engine. The rotor 6 wheels round to a support 7 of the catode 4. The inner cylinder 9 presents an helicoid slit f which together with the parallel slits e of the outer cylinder 8 allow the exclusive passing of a filiform beam of X radiations c. The rapide displacement of the parallel slits e of the outer cylinder 8 realises the orizontal sweep of the filiform beam of X radiations c, and the displacement much slower of the helicoid slit f of the inner cylinder 9 achieves the vertical sweep of the filiform beam of X radiations. The horizontal and vertical sweep of the filiform beam of the X radiations c is syncronized with the sweep of the T.V. monitor with aid of a system of synchronizing. The transformation of the signals of X radiations into video signals is achieved into an ordinary T.V. chain with a strengthening image device (image amplifier) or into a photomultiplier scintilator.

Figure 4:
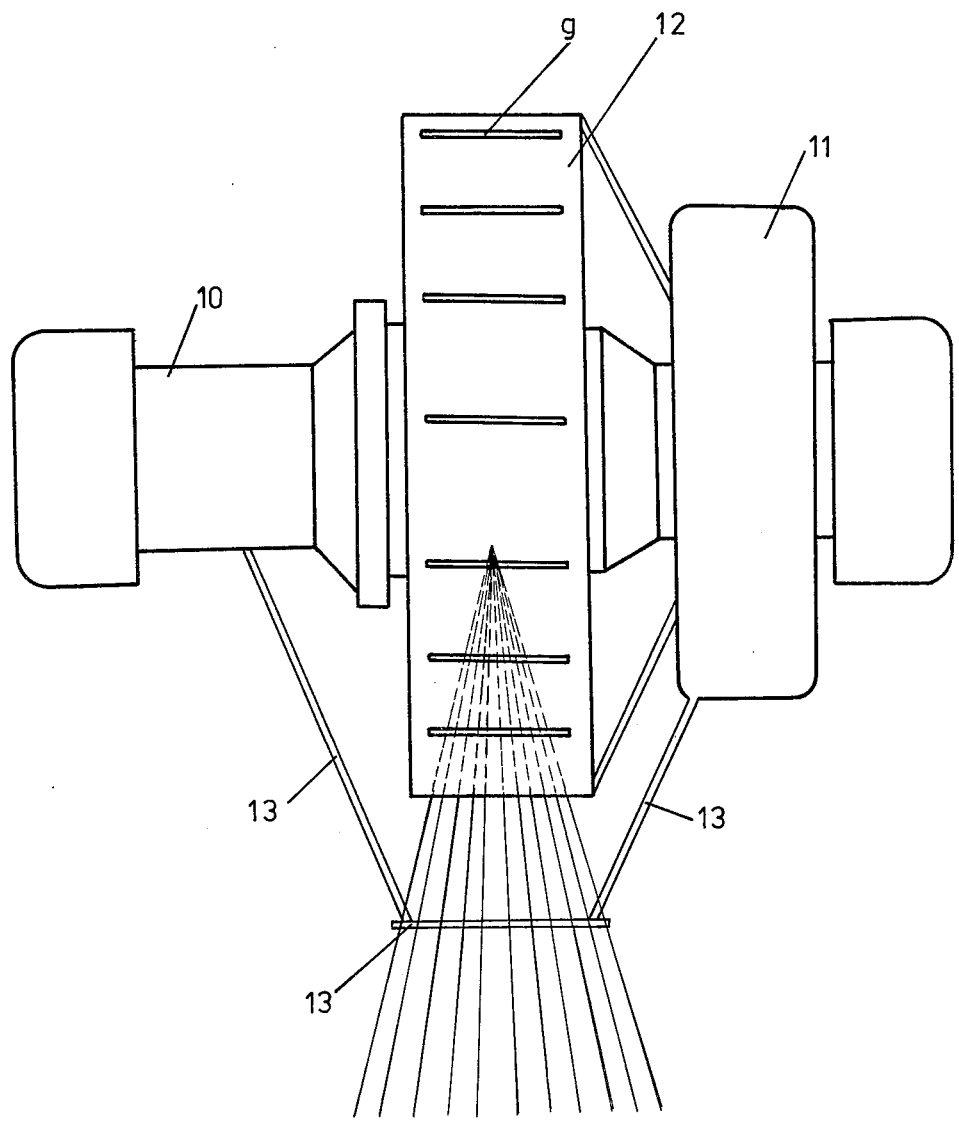

The 4th example in connection with FIG. 4, which represents a principle scheme of the radiodiagnosis installation according to the invention into a fourth form of achievement in which a radioopaque device is placed out of the radiodiagnosis tube, which radioopaque device has a cylindrical form. The installation is made-up of a cupola 10 with a rotary anode radiodiagnosis tube (non figurated, an electric engine 11 which drows a radioopaque cylinder 12 made-up of a metal with high atomic weight. The radioopaque cylinder 12 is provided with linear slits g parallel between them and slight oblique with respect to the axle of the radiodiagnosis tube. The distance between two slits g corresponds to the radiologic image surface. The number of slits g which passed in front of the X radiations beam per time unit is synchronized with the number of frames from the monitor. It is obtained a lamellar beam of X radiations. The cupola 10 is fixed on the stand of the radiodiagnosis apparatus by a support, 13. This variety is utilized with an image amplifier and T.V. chain and there is used a conventional radiodiagnosis installation at which the radioopaque device is added.

Figure 5:
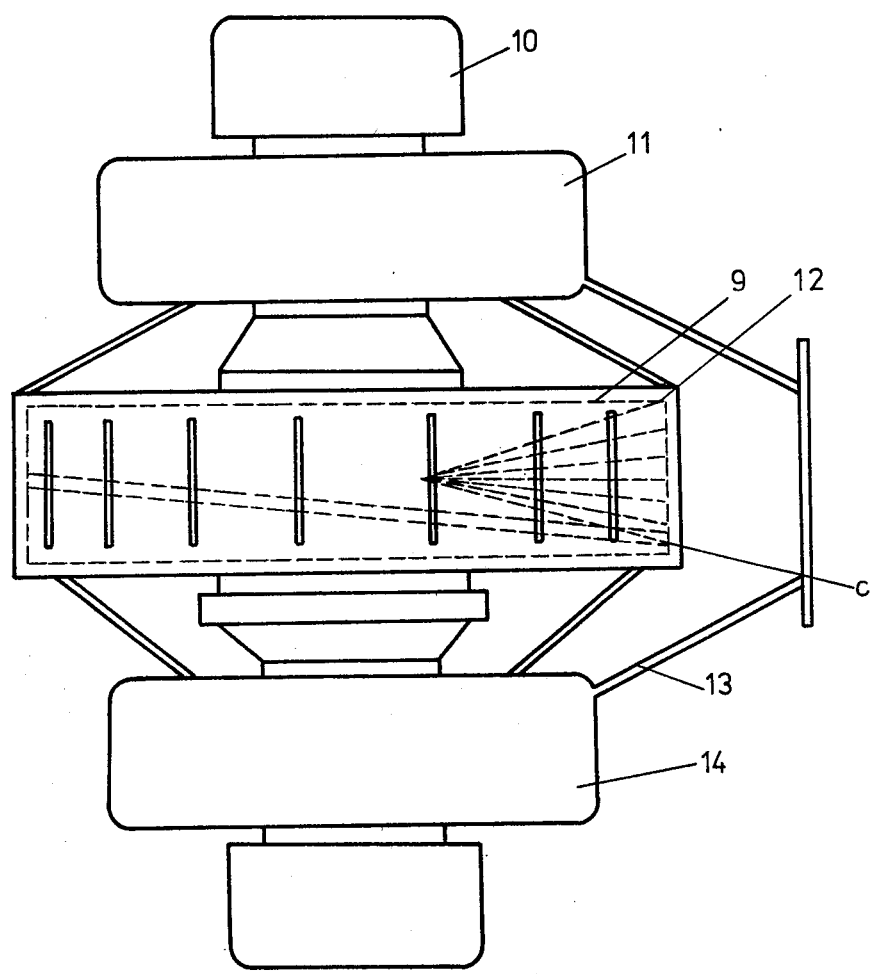

The 5th example, in connection with FIG. 5 wich represents a principle scheme of the radiodiagnosis installation according to the invention in a fifth form of achievement. This variety is different of that described in the fourth example by that it uses two radioopaques cylinders, one outer 12 and one inner 15 and two electric engines 11, 14 which wheel round the two said radioopaques cylinders 12, 15. The outer radioopaque cylinder 15 is provided with slits g vertical and parallel between them, but slight oblique with respect to the axle of the radiodiagnosis tube. Said slits g, during of the whirling of the outer radioopaque cylinder 12 achieve the horizontal sweep of the X radiations beam c. The inner radioopaque cylinder 15 presents an helicoid slit f which during of the whirling of the radioopaque cylinder 15 achieves the vertical sweep of the X radiations beam. The transformation of the X radiations signals into video signals is made with the aid of an image amplifier with T.V. camera or with a scintilator with photomultiplier.

Figure 6:
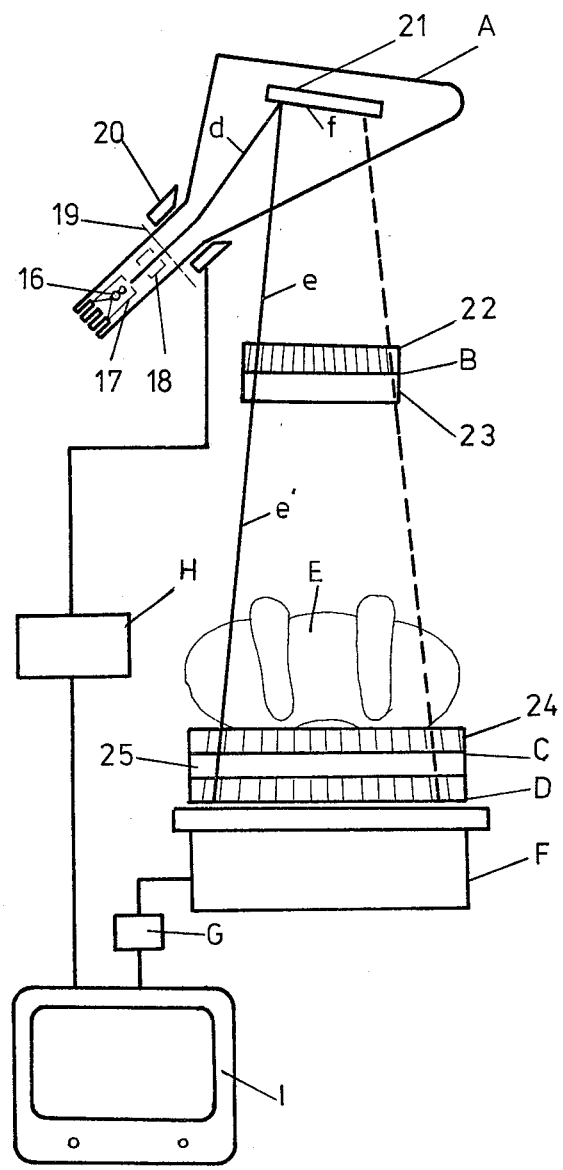

The 6th example in connection with FIG. 6 represents principle scheme of the radiodiagnosis installation according to the invention into a sixth form of achievement, wich takes in a radiodiagnosis tube A having a cathode 16 a Wehnelt cylinder 17, a focussing and acceleration system 18, a control grid 19, deflection coils 20, and a fixed anode 21. The fixed anode 21 of metal with high atomic weight and high melting point, for example tungsten, has a bombardment surface f plane, concave or of another geometric form. In this radiodiagnosis tube is achieved the horizontal and vertical sweep of a cathodic filiform beam d, on the surface f of the fixed anode 21, where X radiations with sweep emission point e arise. The X radiations e pass through three antidiffusion systems B, C, D, which have the purpose to allow the passing, from each point of the fixed anode 21, by one filiform X radiations beams which pass through the examined object E, placed between the antidiffusion systems D and C. The X radiations beam e therefore are turned into a filiform X radiation beam e. In certain cases a single antidiffusion system or two antidiffusion systems are utilized. The X radiations filiform beam e', after the passing through the antidiffusion system D arrives at a photomultiplier scintillator F, where the swept X radiations e', are turned into video signals, which video signals are amplified into an amplifier 6 and order the image forming into a T.V. monitor I. The sweep of the filiform electrons beam d of the radiodiagnosis tube A is sincronized with the sweep of the T.V. monitor I by a generator of sincronizing H. The intensity of the electrons beam of the radiodiagnosis tube A is adjusted with aid of the control grid 19 by a control system with correction programme. The antidiffusion system B and C are formed each by two antidiffusion grids 22,23,24,25, made-up of lamellas, fibres or tubes among which remain tight and long spaces with the axle orientated in the direction of the swept filiform x radiations beams e'. These antidiffusion grids can be mobile too. The antidiffusion system D placed in connection with the photomultiplier scintilator F is made up of optic fibres of cylindric form, prismatic, tubular or another form having the axle orientated in the direction of the filiform X radiations beams e'. The optic fibres are made-up of substances transparent at light with high atomic weith wich fibres take in their inner or/and between them luminiscent substance. The X radiations penetrate through the luminiscent substance situated between the fibres. In this luminiscent substance on the entire length of the fibres, the X radiant energy is transformed in light with a better output, light which is then lead through the optic fibres at the photomultiplier surface. In this antidiffusion system D the optic fibres work like a antidiffusion grid and in the same time like optic fibre. The luminiscent substance situated in transparent medium to light works like a X radiations-light translator.

Figure 7:
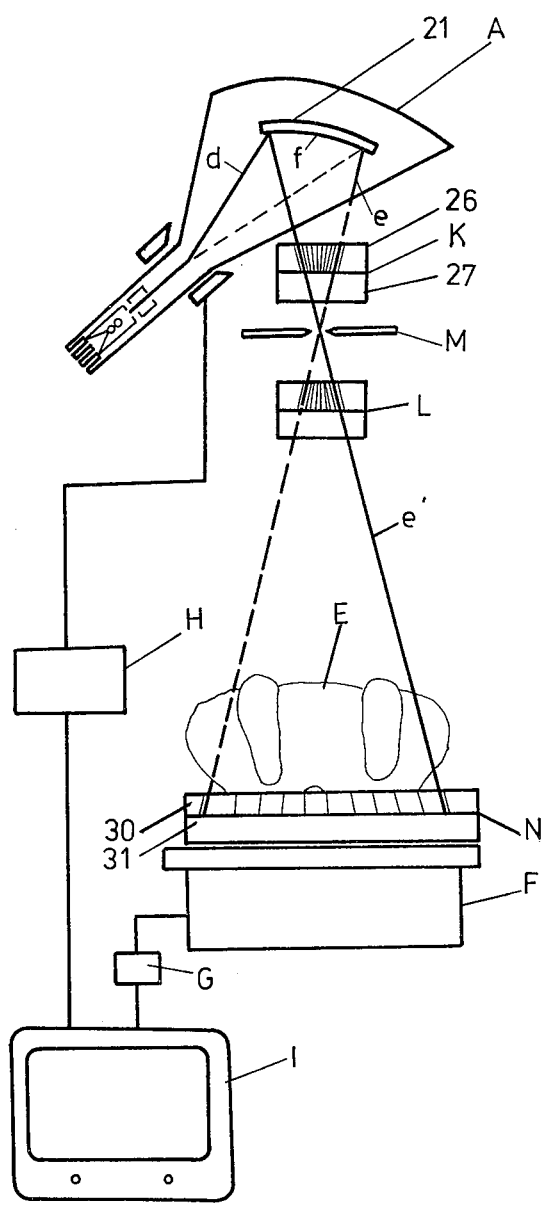

The 7th example in connection with FIG. 7 which represents a principle scheme of a radiodiagnosis installation according to the invention into a seventh form of achievement which takes in a radiodiagnosis tube A, similar with that described in the 6th example and represented in FIG. 6. The X radiations e emitted by the surface f of the fixed anode 21 swept by the filiform beam d pass through four antidiffusion systems of which one M is made-up of a radioopaque plate of metal with high atomic weight provided with a channel made up of one or two cones which touch at the peak spearing a punctiform orifice. In these cones or in their imediate approach may be placed two fixed or mobile antidiffusion grids which converge to the punctiform orifice (non represented). A second antidiffusion system K is placed between the fixed anode 21 and the radioopaque plate M. A third antidiffusion system L is placed between the radioopaque plate M and the examined object E. A fourth antidiffusion system N is placed between the examined object E and the sensitive surface of a photomultiplier scintillator F. The antidiffusion systems K,L,M,N, include each two antidiffusion grids 26,27,28,29,30,31, (the grids of the systems M are not figurated). Said grids are made-up of lamellas, fibres and tubes of substances with high atomic weight which have long and tight spaces between them of which axle is oriented to the swept points from the bombarded surface F of the fixed anode 21 and to the punctiform orifice of the radioopaque plate M. The antidiffusion systems K.L.M.N. have the purpose of the transformation of the X radiations beams e emited by the fixed anode 21 in filiform X radiations beams e'. There may be used one or more of the antidiffusion systems K,L,M,N. The X radiations filiform beams arrive at the sensitive surface of the photomultiplier scintilator F, where said radiations are turned into video-signals, which are amplified by an amplifier 6 and order the image forming into a T.V. monitor I'. The sweep of the cathodic filiform beam d of the radiodiagnosis tube A is synchronized with the sweep of the electrons beam of the T.V. monitor I by a generator of synchronizing H.

Figure 8:
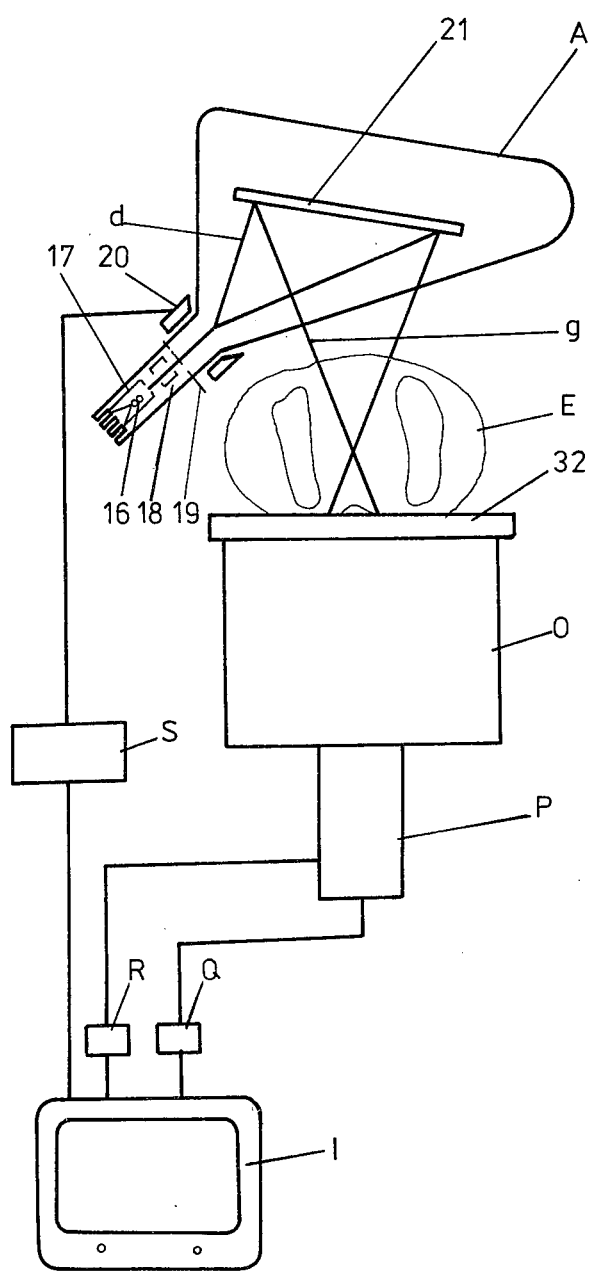

The 8th example in connection with FIG. 8, which represents a principle scheme of a sweep radiodiagnosis installation used for tomoscopy and electronic tomography, according to the invention. The installation includes a radiodiagnosis tube A having in a cathode 16 a Wehnelt cylinder 17 a focussing and acceleration system 18 a grid 19 a deflection system 20 and a fixed anode 21. IN this radiodiagnosis tube A is achieved the horizontal and vertical sweep of the cathodic beam d focused on the fixed anode 21, where X radiations g arise with swept emission point. This X radiations beam g passes through the examined object E and arrives at a photocathode 32 of the mage amplifier F which together with the camera O turns the X radiations into video-signals, which are amplified into an amplification system P and order the image forming in a T.V. monitor I. A sistem of syncronizing R synchronizes the sweep of the cathodic beam (non-represented) of the camera O with the cathodic beam (non represented) of the T.V. monitor I. Said monitor is provided with a supplementary deflection device (non represented) which displaces horizontaly and verticaly the entire image from the T.V. monitor I in the inverse direction with respect to the image displacement from the T.V. monitor I during of the X radiations beam sweep. The amplitude of horizontal and vertical displacement achieved by the supplementary deflexion system can be adjusted by known means. A second system of synchronising R synchronizes the sweep of the cathodic beam d of the radiodiagnosis tube A with the image displacement achieved into the T.V. monitor I by the supplementary deflection system.

Figure 9:
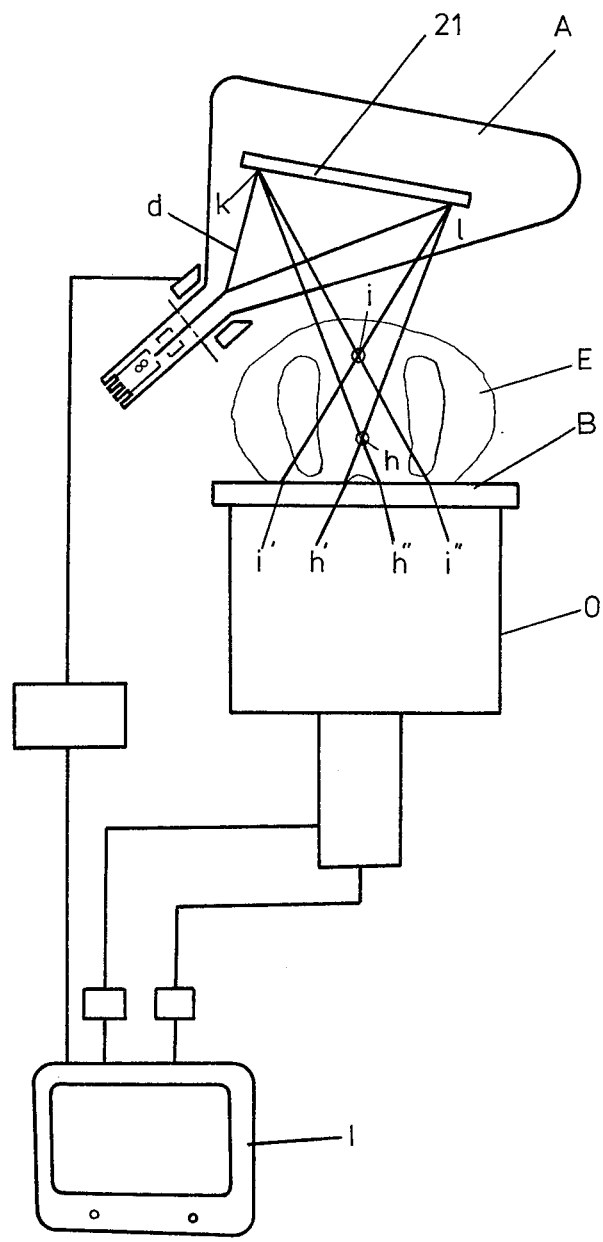
Figure 10:
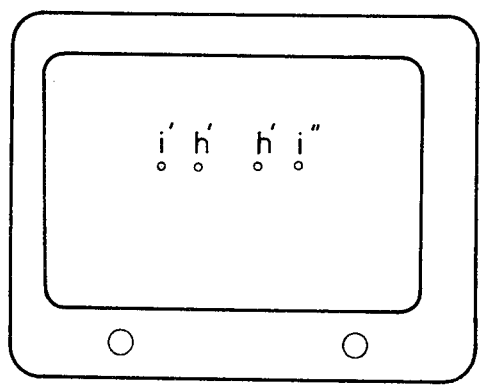
Figure 11:
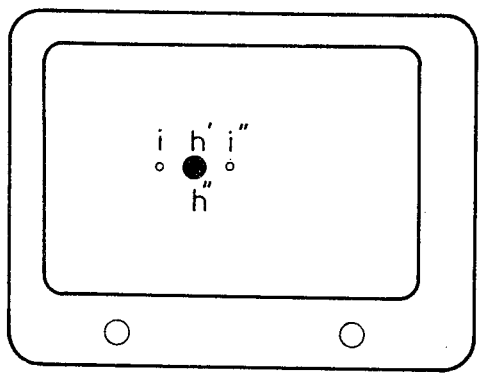
Figure 12:
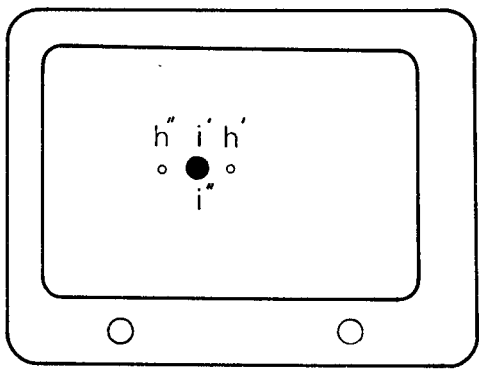

In another variant the displacement of the entire image may be achieved by a supplementary deflection system mounted on the camera T.V., O. The FIG. 9 represents a scheme in connection with the image forming on the photocathode 32 of the image amplifier N. One takes two points of the examined object E placed in different planes. These points are noted with h and i and are selected so that during a horizontal complete sweep of the cathodic beam on the fixed anode 21 from the point k to point 1 the point image h should be displaced on the photocathode 32 of the image amplifier F from h' to h". At the same time the point image i, which is placed into a remote plane from the photocathode 32 should be displaced from i' to i" which represents a distance longer than h'h" on the screen of the T.V. monitor I represented in the FIG. 10 these point will appear in motion and the said i' point displaces to i" and said h' point displaces to h". The T.V. monitor I has a supplementary deflection system synchronized with the sweep of the cathodic beam d (FIG. 8) of the radiodiagnosis tube A. This supplementary deflection system operates so that the entire image of the T.V. monitor displaces on an equal distance and in the inverse sense of the displacement of the image point i from i' to i" (FIG. 11). As a rezultant of these two displacements the point i will remain in the same place on the screen of the T.V. monitor I all the time of the sweep, and has a punctiform sharp image, and the point h is displaced on a distance longer than the inverse displacement of the entire image. For this reasson its displacement will not be entirely compensated by the supplementary deflection of all the image and describes on the T.V. monitor screen I displacements of sweep between h' and h" (FIG. 11). In this way the point image i on the T.V. monitor screen I will give a sharp punctiform image, the point image h on the T.V. monitor screen I sweeps as a resultant of the oscillation between the points h' and h". The T.V. monitor I has a supplementary deflection system in the vertical sense also, which operates in the same way as the horizontal deflection system. Therefore the point image h will sweep not only in the horizintal sense but combined in the horizontal and vertical sense, that is in surface. In the case that this supplementary deflection system will be adjusted so that the entire image of the T.V. monitor I should be displaced in the inverse sense with the displacement of the point h from h' to h" at a equal distance, the displacement of the point h will be compensated. In this case the image of the point h will remain sharp, punctiform and the point i is swept from i' to i" and its image wipes (FIG. 12).

All the points situated in the plane of the point h have approximately the same distance from the photocathode, therefore the entire plane of the point h has a sharp image, the image of the plane of the point i practically disapears. By variations of the amplitude of the supplementary deflection one can show successivelly all the layers of the examined object E (FIG. 8). There is a first system of syncronizing between the sweep of camera T.V., D and the T.V. monitor I and a second system of synchronizing H between the sweep of the electrons beem d of the radiodiagnosis tube A and the sweep obtained by the supplementary deflection system of the T.V. monitor I. Between the two systems of syncronizing there is a fixed or adjustable time ratio.

The T.V. camera O (FIG. 8) turns the X radiations image into video-signals which may command simultaneously the image of more T.V. monitors (non figurated), which are adjusted for showing different layers. If the images of the different layers are displayed on different planes corresponding to the examined object, a tridimensional image is obtained.

The 9th example represents the fitting of a memory system (non figurated) to the installation of the 8th example, between the T.V. camera 8 and the T.V. monitor I, memory system in which the information elements obtained during the sweep of the X radiations are recorded. These information elements will be reproduced on the T.V. monitor I. By the aid of the supplementary deflection system of the T.V. monitor I the displacement of the image of the points from the dezirable plane of the examined object E will be compensated, obtaining a sharp image of the dezirable plane. By the adjustment of the displacement amplitude of the image on the monitor one can see succesivelly the image of all the layers. In case of utilizing more T.V. monitors these layers can simultaneously be seen or one can obtain an tridimensional image.

The installation according to the invention has the following advantages:

reduction practically of the whole radiologic irradiation of the examined persons and of the attending staff;

reduction practically of the whole secondary radiations;

improvement of the radiologic image quality;

achievement of an improved tomographic image with the wipe in surface achievement of tomographic images by electronic means, without mechanic components;

easy passage from the tomoscopic image to a target tomography;

simultaneous observation of different layers of an object;

electronic achievement of a tridimensional image;

information store into a memory of the different layers of the examined object;

high fiability with low cost price and easy maintaince;

possiblity of data processing on a computer.

What is claimed is:

1. A radiodiagnosis-tomography apparatus comprising:
   a radiodiagnosis tube including:
      a sealed envelope having a cylindrical axially extending first portion, a cylindrical axially extending second portion, coaxial with said first portion and of a larger diameter than said first portion, and a third portion coaxial with said first and second portions and of a smaller diameter than said second portion,
      a rotary anode in said second portion,
      a rotatable body forming part of an electric motor in said third portion operatively connected to said anode for rotating same,
      a cathode in said second portion extending axially from said first portion and juxtaposed with said anode and cooperating therewith to produce an outwardly directed X-ray beam sweeping around said second portion, and
      an annular radio-opaque shield of a metal of high atomic weight and high melting point disposed in said second portion and surrounding said anode, said shield being formed with at least one opening and being provided with means for rotating said shield about a common axis of said envelope and said anode for sweeping a filiform pencil of X-ray radiation derived from said beam across a patient juxtaposed with said second portion of said envelope:
   a transducer responsive to X-ray radiation spaced from said second portion and intercepting the portion of said pencil of X-ray radiation traversing the patient, producing signals adapted to generate a television display; and
   means responsive to said signals and synchronized with the rotation of said shield for displaying a series of points representing a tomographic image of the patient.

2. The apparatus defined in claim 1 wherein said shield is connected to said body for rotation with said anode.

3. The apparatus defined in claim 1 wherein the means for rotating said shield comprises another rotary body forming part of an electric motor and disposed in said first portion of said envelope.

4. The apparatus defined in claim 1 wherein said transducer includes a photomultiplier scintillator.

5. The apparatus defined in claim 1, further comprising an array of elongated elements composed of a material of high molecular weight and having axes directed at corresponding points of the sweep of the pencil.

6. The apparatus defined in claim 1, 2, 3, 4 or claim 5 wherein said opening is one of a plurality of slits.

7. The apparatus defined in claim 1, 2, 3, 4 or 5 wherein said opening is one of a plurality of holes disposed in a helical pattern.

* * * * *